(12) United States Patent
Suzuki et al.

(10) Patent No.: US 11,410,774 B2
(45) Date of Patent: Aug. 9, 2022

(54) COMPUTER SYSTEM, COGNITIVE FUNCTION EVALUATION METHOD, AND PROGRAM

(71) Applicant: HITACHI, LTD., Tokyo (JP)

(72) Inventors: Daisuke Suzuki, Tokyo (JP); Satoru Hanzawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 743 days.

(21) Appl. No.: 16/224,431

(22) Filed: Dec. 18, 2018

(65) Prior Publication Data

US 2019/0189279 A1 Jun. 20, 2019

(30) Foreign Application Priority Data

Dec. 20, 2017 (JP) .............................. JP2017-243788

(51) Int. Cl.
*G16H 50/20* (2018.01)
*A61B 5/00* (2006.01)
*A61B 5/022* (2006.01)
*A61B 5/01* (2006.01)

(52) U.S. Cl.
CPC .......... *G16H 50/20* (2018.01); *A61B 5/0022* (2013.01); *A61B 5/4088* (2013.01); *A61B 5/7275* (2013.01); *A61B 5/01* (2013.01); *A61B 5/022* (2013.01)

(58) Field of Classification Search
CPC .... G16H 50/20; A61B 5/4088; A61B 5/7275; A61B 5/0022
See application file for complete search history.

(56) References Cited

U.S. PATENT DOCUMENTS

| | | | | |
|---|---|---|---|---|
| 2009/0287064 | A1* | 11/2009 | Dougherty, Jr. | ........ G16Z 99/00 600/300 |
| 2011/0166884 | A1* | 7/2011 | Lesselroth | ............. G06Q 10/06 705/3 |
| 2011/0236864 | A1* | 9/2011 | Ashford | ............... A61B 5/4088 434/236 |
| 2013/0132110 | A1* | 5/2013 | Nagaoka | ................ G16H 50/20 705/2 |
| 2017/0095193 | A1* | 4/2017 | Shin | ......................... A61B 5/16 |

FOREIGN PATENT DOCUMENTS

JP        2016-071897 A        5/2016

* cited by examiner

*Primary Examiner* — John P Go
(74) *Attorney, Agent, or Firm* — Volpe Koenig

(57) ABSTRACT

A computer system supplies a health service using body information measured by a measurement instrument. The computer system includes a computer that includes an analysis unit analyzing memory of a user. The analysis unit analyzes an error pattern based on a history of a matching-determination process for body information transmitted by the measurement instrument and body information input by the user, calculates a first evaluation value for evaluating a cognitive function based on an analysis result of the error pattern, analyzes an action pattern related to an input action of body information of the user, calculates a second evaluation value for evaluating the cognitive function based on an analysis result of the action pattern, and evaluates the cognitive function of the user based on the first evaluation value and the second evaluation value.

15 Claims, 9 Drawing Sheets

| MEASUREMENT TIME 501 | ID 502 | TYPE OF MEASUREMENT INSTRUMENT 503 | TYPE OF BODY INFORMATION 504 | BODY INFORMATION 505 | ELAPSED TIME 506 | INPUT TIME 507 | ... |
|---|---|---|---|---|---|---|---|
| 2017.04.15 07:30:20 | 0011 | BODY COMPOSITION METER | BODY WEIGHT | 67.4 | 3.2 | 00:03:21 | ... |
| 2017.04.15 07:30:20 | 0011 | BODY COMPOSITION METER | BODY FAT RATIO | 22.0 | 3.9 | 00:03:51 | ... |
| 2017.04.15 07:30:20 | 0011 | BODY COMPOSITION METER | BONE DENSITY | 15 | 4.2 | 00:04:12 | ... |
| 2017.04.15 07:35:42 | 0012 | SPHYGMOMANOMETER | SYSTOLIC BLOOD PRESSURE | 112 | 2.2 | 00:05:35 | ... |
| 2017.04.15 07:35:42 | 0012 | SPHYGMOMANOMETER | DIASTOLIC BLOOD PRESSURE | 76 | 2.3 | 00:05:41 | ... |
| 2017.04.15 07:35:42 | 0012 | SPHYGMOMANOMETER | PULSE RATE | 56 | 2.5 | 00:05:55 | ... |
| 2017.04.15 07:41:11 | 0013 | ACTIVITY METER | NUMBER OF STEPS | 241 | 5.3 | 00:03:46 | ... |
| 2017.04.15 07:41:11 | 0013 | ACTIVITY METER | NUMBER OF RUNNING STEPS | 30 | 6.2 | 00:04:08 | ... |
| 2017.04.15 07:41:11 | 9013 | ACTIVITY METER | MEASUREMENT PATTERN INFORMATION | - | - | - | ... |
| 2017.04.15 07:41:11 | 9000 | PORTABLE TERMINAL | MEASUREMENT PATTERN INFORMATION | - | - | - | ... |
| ... | ... | ... | ... | ... | ... | ... | ... |

| MEASUREMENT TIME 501 | ID 502 | TYPE OF MEASUREMENT INSTRUMENT 503 | TYPE OF BODY INFORMATION 504 | ... | NUMBER OF CORRECTIONS 508 | MATCHING RESULT 509 | NUMBER OF REPETITIONS 510 | NUMBER OF ITEMS 511 |
|---|---|---|---|---|---|---|---|---|
| 2017.04.15 07:30:20 | 0011 | BODY COMPOSITION METER | BODY WEIGHT | ... | 0 | TRUE | - | - |
| 2017.04.15 07:30:20 | 0011 | BODY COMPOSITION METER | BODY FAT RATIO | ... | 0 | TRUE | - | - |
| 2017.04.15 07:30:20 | 0011 | BODY COMPOSITION METER | BONE DENSITY | ... | 2 | TRUE | - | - |
| 2017.04.15 07:35:42 | 0012 | SPHYGMOMANOMETER | SYSTOLIC BLOOD PRESSURE | ... | 0 | TRUE | - | - |
| 2017.04.15 07:35:42 | 0012 | SPHYGMOMANOMETER | DIASTOLIC BLOOD PRESSURE | ... | 0 | FALSE | - | - |
| 2017.04.15 07:35:42 | 0012 | SPHYGMOMANOMETER | PULSE RATE | ... | 0 | TRUE | - | - |
| 2017.04.15 07:41:11 | 0013 | ACTIVITY METER | NUMBER OF STEPS | ... | 3 | TRUE | - | - |
| 2017.04.15 07:41:11 | 0013 | ACTIVITY METER | NUMBER OF RUNNING STEPS | ... | 2 | TRUE | - | - |
| 2017.04.15 07:41:11 | 9013 | ACTIVITY METER | MEASUREMENT PATTERN INFORMATION | ... | - | - | 2 | - |
| 2017.04.15 07:41:11 | 9000 | PORTABLE TERMINAL | MEASUREMENT PATTERN INFORMATION | ... | - | - | - | 8 |
| ... | ... | ... | ... | ... | ... | ... | ... | ... |

COMPUTER SYSTEM, COGNITIVE FUNCTION EVALUATION METHOD, AND PROGRAM

CLAIM OF PRIORITY

The present application claims priority from Japanese patent application JP 2017-243788 filed on Dec. 20, 2017, the content of which is hereby incorporated by reference into this application.

BACKGROUND OF THE INVENTION

1. Field of the Invention

The present invention relates to a cognitive function evaluation technology for diagnosing dementia in a system that provides a health service.

2. Description of Related Art

In recent years, people in which dementia occurs have increased with advancement of aging society. Accordingly, an increase in medical expenses and a lack of resources necessary for nursing are problems.

An onset ratio of dementia also increases with an increase in age. There are various kinds of dementia. Of the dementia, Alzheimer dementia occupies a large onset ratio. It has been known that a progress of Alzheimer dementia can be delayed when appropriate diagnosis and treatment are executed at an early stage after Alzheimer dementia occurs. Therefore, it is important to find an outbreak of dementia early.

A difficulty to find the outbreak of dementia early is that people are rarely conscious. Since symptoms of dementia gradually progress in many cases, people can rarely notice changes of their own although dementia breaks out. In addition, when symptoms of dementia progress, people may not normally determine their own symptoms.

The symptoms of dementia are pointed out from people living together in many cases. However, when people living together notice symptoms of dementia, the symptoms of dementia have progressed in many cases.

As methods of finding an outbreak of dementia, revised version of Hasegawa's Dementia Scale (HDS-R) and Mini-Mental State Examination (MMSE) are frequently used. However, it is not practical for people to carry out examinations based on the above-described methods daily.

A system that reevaluates an improvement effect of dementia autonomously in order for a user to execute measurement of cognition and a rehabilitation training of dementia alone is known (for example, see JP-A-2016-071897). JP-A-2016-071897 discloses that "measurement of cognition and a rehabilitation training of dementia are executed using a plurality of game applications corresponding to core symptoms of dementia, a mode selection unit that selects a measurement mode and a training mode is included, and in the measurement mode, a function of selecting a game corresponding to a level of current cognition of a facility user according to each evaluation index, calculating a cognition evaluation value from a game execution result and recording the cognition evaluation value in a user log, and calculating a recognition level evaluation value from the cognition evaluation value of each evaluation index and updating the level of cognition of the facility user is provided; in the training mode a game selected by the facility user from games corresponding to the level of current cognition of the facility user is caused to be executable; and a report is generated based on the user log."

Even when the technology disclosed in JP-A-2016-071897 is used, it is considered that it is difficult for people, in particular, people in which dementia does not occur to use the system disclosed in JP-A-2016-071897 daily.

Since the method of examining dementia in the related art is executed using an examination method or system specialized for evaluation of a cognitive function, there is a problem that it is difficult to carry out examination daily and people uninterested in the examination do not carry out the examination actively.

SUMMARY OF THE INVENTION

The invention provides a system, a method, and a program realizing evaluation of a cognitive function which can be used by various users without using an examination method and system specialized for evaluation of the cognitive function.

A representative example of the invention disclosed in the present specification is as follows. That is, a computer system supplies a health service using body information of a user measured by a measurement instrument. The computer system includes a computer that includes an analysis unit analyzing a cognitive function of the user. The computer includes a processor, a memory connected to the processor, and a network interface connected to the processor. The processor is connected to be accessible to a storage device that stores first body information which is body information transmitted by the measurement instrument. The analysis unit acquires the first body information and second body information which is body information presented by the measurement instrument and memorized by the user, executes a matching-determination process of determining whether the second body information matches the first body information, generates input action information which is information regarding an input action of the second body information by the user, registers the first body information in the storage device in association with a result of the matching-determination process and the input action information, acquires histories of the result of the matching-determination process and the input action information from the storage device, analyzes an error pattern related to the number of times the first body information different from the second body information is input based on the history of the result of the matching-determination process and calculates a first evaluation value for evaluating the cognitive function based on an analysis result of the error pattern, analyzes an action pattern related to the input action of the user based on the history of the input action information and calculates a second evaluation value for evaluating the cognitive function based on an analysis result of the action pattern, and evaluates the cognitive function of the user based on the first evaluation value and the second evaluation value.

According to an aspect of the invention, the cognitive function (memory) can be evaluated without imposing a burden on the user in a health service for ascertaining a health state. Other problems, configurations, and advantages are revealed in the description of the following embodiments.

DESCRIPTION OF EMBODIMENTS

Hereinafter, embodiments of the invention will be described with reference to the appended drawings. The same reference numerals are given to common portions in each drawing.

First Embodiment

Figure 1:
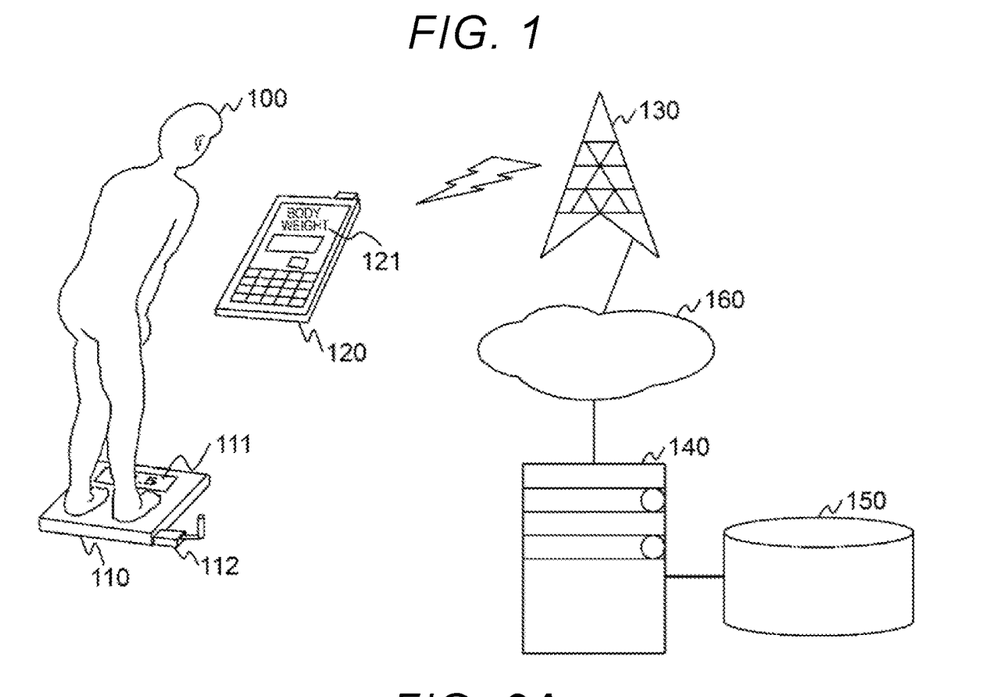
FIG. 1 is a diagram illustrating a configuration example of a computer system according to a first embodiment.
Figure 2A:
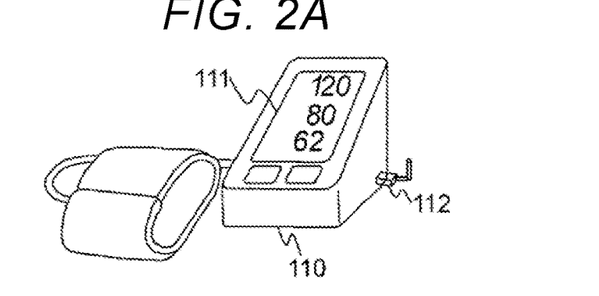
FIG. 2A is a diagram illustrating an example of a measurement instrument according to the first embodiment.
Figure 2B:
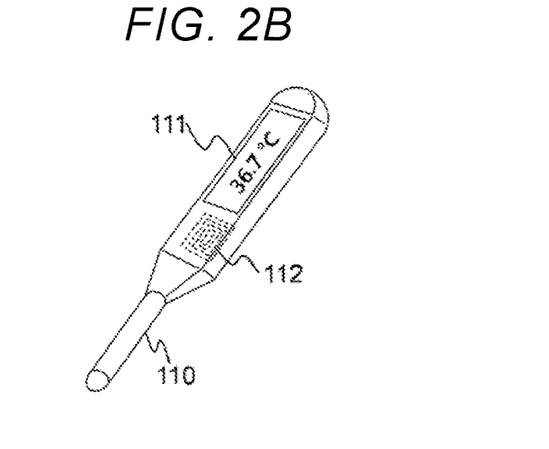
FIG. 2B is a diagram illustrating an example of a measurement instrument according to the first embodiment.
Figure 2C:
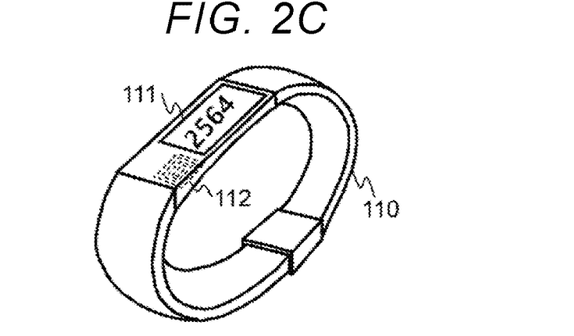
FIG. 2C is a diagram illustrating an example of a measurement instrument according to the first embodiment.
Figure 3:
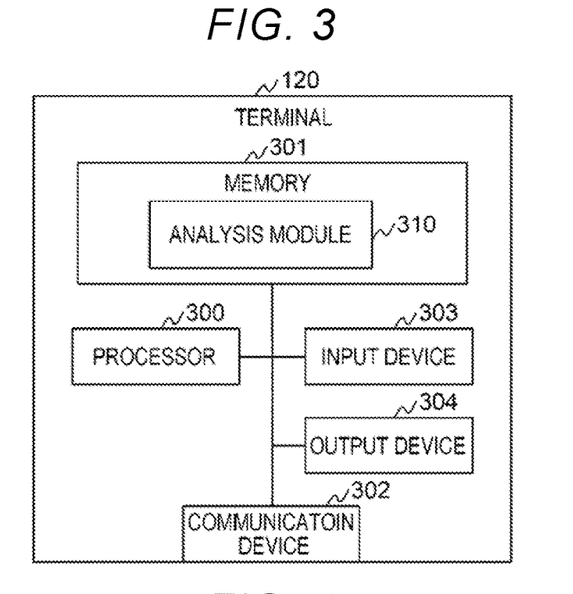
FIG. 3 is a diagram illustrating an example of a hardware configuration and a software configuration of a terminal according to the first embodiment.
Figure 4:
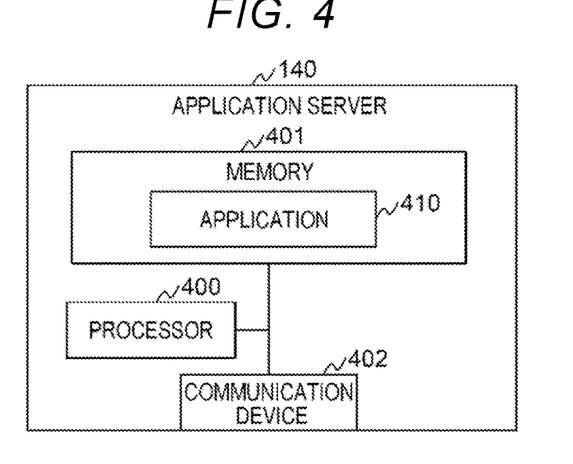
FIG. 4 is a diagram illustrating an example of a hardware configuration and a software configuration of an application server according to the first embodiment.

FIG. 1 is a diagram illustrating a configuration example of a computer system according to a first embodiment. FIGS. 2A, 2B, and 2C are diagrams illustrating examples of device forms of measurement instruments 110 according to the first embodiment. FIG. 3 is a diagram illustrating an example of a hardware configuration and a software configuration of a terminal 120 according to the first embodiment. FIG. 4 is a diagram illustrating an example of a hardware configuration and a software configuration of an application server 140 according to the first embodiment.

The computer system includes a measurement instrument 110, a terminal 120, a base station 130, an application server 140, and a database 150.

The application server 140 and the database 150 according to the present embodiment form a system that manages control and information of a health service. In the health service according to the present embodiment, body information measured using the measurement instrument 110 is managed, a health state based on the body information is managed, and a cognitive function is evaluated. A user 100 can further ascertain an outbreak risk of dementia in addition to a change in the body information and a health state by using the health service. In the evaluation of the cognitive function according to the present embodiment, memory which is one of the cognitive functions is evaluated.

The base station 130 and the application server 140 are connected via a network 160. The network 160 is a wide area network (WAN), a local area network (LAN), or the like. The terminal 120 and the base station 130 are connected via a wireless network (not illustrated). The application server 140 and the database 150 are connected directly or via a network.

The measurement instrument 110 is a device that measures body information of the user 100. FIG. 1 illustrates a weight meter that measures a body weight and a body composition as body information as an example of the measurement instrument 110. The invention is not limited to the type of measurement instrument 110. For example, as the measurement instrument 110, a sphygmomanometer illustrated in FIG. 2A, a thermometer illustrated in FIG. 2B, and an activity meter illustrated in FIG. 2C are considered. Note that the activity meter is a device that measures the number of steps, the number of runs, a heart rate, an exercise amount, a sleep time, or the like as the body information. A pedometer (not illustrated) measuring the number of steps as body information may be used as the instrument meter 110.

The measurement instrument 110 according to the first embodiment includes a display screen 111 and a communication device 112. The measurement instrument 110 includes hardware such as an arithmetic device such as a processor and a storage device such as a memory.

The display screen 111 is a screen on which body information is displayed. In the present embodiment, the user 100 memorizes the body information displayed on the display screen 111 and inputs the body information to the terminal 120. The communication device 112 is a device that communicates with an external device such as the terminal 120.

Note that when the measurement instrument 110 is a weight meter or a heart rate meter, the communication device 112 is mounted as an electronic circuit contained in an externally attached device or a device. When the measurement instrument 110 is a thermometer or an activity meter, the communication device 112 is mounted as an electronic circuit contained in a device.

In the present embodiment, the measurement instrument 110 notifies the user 100 of the body information using the display screen 111, but the present embodiment is not limited thereto. For example, the measurement instrument 110 may include a sound reproduction device and notify the user 100 of the body information as a sound from the sound reproduction device. In this case, the user 100 memorizes the body information acquired as the sound and input the body information to the terminal 120.

The terminal 120 is a device such as a mobile phone, a smartphone, or a tablet terminal. Here, a hardware configuration and a software configuration of the terminal 120 will be described with reference to FIG. 3.

The terminal 120 includes a processor 300, a memory 301, a communication device 302, an input device 303, and an output device 304. Each piece of hardware is mutually connected via an internal bus.

The processor 300 is an arithmetic device that executes a program stored in the memory 301. When the processor 300 executes a process in accordance with the program, the processor 300 operates as a functional unit (module) that realizes a specific function. In the following description, when the functional unit is described in a subject, it is indicated that the processor 300 executes the program to realize the functional unit.

The memory 301 is a storage device that stores a program which is executed by the processor 300 and information which is used by the program. The memory 301 includes a work area which is temporarily used by a program.

The memory 301 of the terminal 120 stores a program that realizes an analysis module 310. The analysis module 310 executes a process of evaluating memory so that the user can ascertain an outbreak risk of dementia.

The communication device 302 is a device that communicates with an external device. The communication device 302 is, for example, a network interface card (NIC).

The input device 303 is a keyboard, a mousse, a touch panel, or the like. The output device 304 is a display, a touch panel, or the like.

The application server 140 is a computer that realizes various functions supplied by the health service. Here, a hardware configuration and a software configuration of the application server 140 will be described with reference to FIG. 4.

The application server 140 includes a processor 400, a memory 401, and a communication device 402. Each piece of hardware is mutually connected via an internal bus. The processor 400, the memory 401, and the communication device 402 are the same hardware as the processor 300, the memory 301, and the communication device 302.

The memory 401 of the application server 140 stores a program that realizes an application 410. The application 410 executes a process to control the health service. The application 410 according to the present embodiment executes a process of recording body information or the like received from the terminal 120 in the database 150.

The database 150 stores various kinds of information used for the health service. For example, the database 150 is realized using a storage system that includes a controller, a communication device, and a storage device such as a hard disk drive (HDD) or a solid state drive (SSD). Examples of information stored in the database 150 will be described with reference to FIGS. 5A and 5B.

Here, an overview of a process in the computer system according to the first embodiment will be described.

For a person (the user 100) in which dementia does not occur, there is a low probability of erroneous body information being input to the terminal 120, and a time necessary to input body information to the terminal 120 is short and is a substantially constant value. In the following description, a probability of erroneous body information being input to the terminal 120 is referred to as an error ratio.

For people in which dementia occurs, memory (a short-term storage ability) deteriorates. Therefore, it is difficult to memory information even for a short time. Accordingly, since people in which dementia occurs frequently check and correct body information, a time necessary to input the body information become long. In particular, since values such as a weight, a blood pressure, and the like that varies daily are information which is impossible to memorize in advance, it is necessary for people to temporarily memorize the body information at the time of measurement. Accordingly, by analyzing a series of actions in which people memorize body information and input the body information, it is possible to accurately evaluate memory.

When symptoms of dementia become serious, there is a possibility of people ending an input of body information without being aware of inputting erroneous body information. In addition, there is a possibility of people forgetting to input body information. That is, when dementia occurs, the number of times erroneous body information is input increases and a time duration from completion of measurement of body information to start of an input becomes longer. Accordingly, by analyzing a series of actions in which people memorize body information and input the body information, it is possible to accurately evaluate memory.

In the following description, information regarding a series of actions in which people memorize body information and input the body information is described as input action information.

In the computer system according to the first embodiment, as described above, the following process is executed using a relation between memory and actions involved with an input of body information.

First, the user 100 measures body information (a weight) using the measurement instrument 110 (a weight meter). Note that the body information is assumed to be continuously measured. For example, the user 100 measures the body information daily, weekly, or monthly.

The measurement instrument 110 transmits the body information to the terminal 120 using the communication device 112 and displays the body information on the display screen 111. At this time, the analysis module 310 of the terminal 120 starts acquiring input action information. Note that meta-information including a measurement completion time, identification information of the measurement instrument 110, a type of measurement instrument 110, and a type of body information are granted to the body information transmitted to the terminal 120.

The user 100 memorizes the body information displayed on the display screen 111 and inputs the memorized body information to the terminal 120 at any timing.

The analysis module 310 of the terminal 120 displays a registration screen 121 when an operation of inputting the body information is received. The user 100 inputs the body information according to the display of the registration screen 121. At this time, the analysis module 310 generates information regarding the operation of inputting the body information using the registration screen 121 as the input action information.

The analysis module 310 determines whether the body information transmitted by the terminal 120 matches the body information input by the user 100. In the following description, the body information transmitted by the terminal 120 is referred to as first body information and the body information input by the user 100 is referred to as second body information. When it is not necessary to distinguish the first body information and the second body information from each other, the first body information and the second body information are referred to as body information. Information regarding the above-described determination result is referred to as matching information.

The analysis module 310 transmits a registration request including the matching information and the input action information to the application server 140 via the base station 130 and the network 160. The analysis module 310 transmits an acquisition request for acquiring histories of the matching information and the input action information to the application server 140.

When the registration request is received, the application 410 of the application server 140 registers the matching information and the input action information in the database 150. When the acquisition request is received, the application 410 reads the histories of the matching information and the body information of the user 100 from the database 150 and transmits the histories of the matching information and the body information to the terminal 120.

The analysis module 310 executes a memory evaluation process of determining whether an outbreak risk of dementia is high using the histories of the matching information and the body information.

Figure 5A:
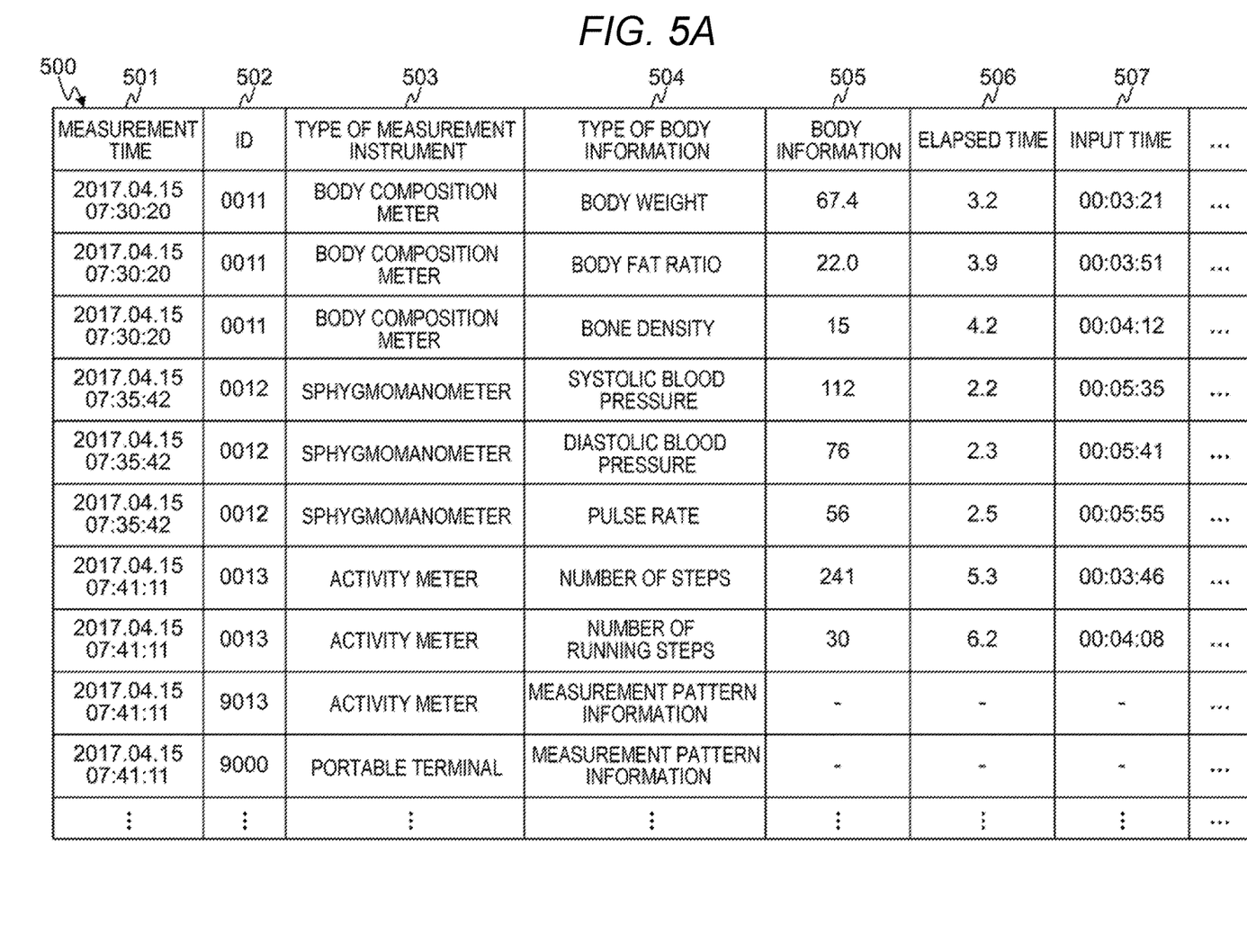
FIG. 5A is a diagram illustrating examples of information stored in a database according to the first embodiment.
Figure 5B:
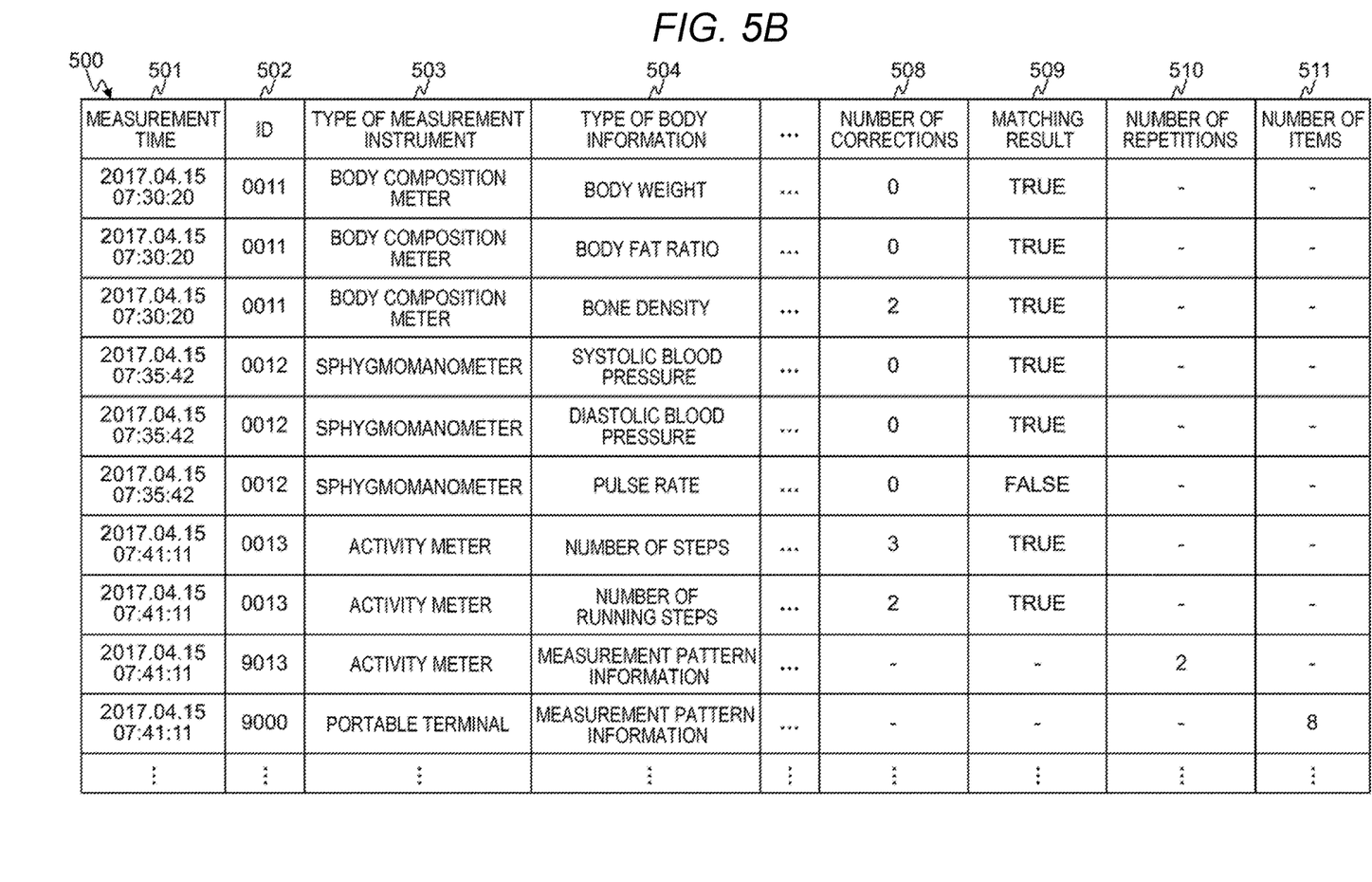
FIG. 5B is a diagram illustrating examples of information stored in a database according to the first embodiment.

Next, information stored in the database 150 will be described. FIGS. 5A and 5B are diagrams illustrating examples of information stored in the database 150 according to the first embodiment.

The database 150 according to the first embodiment stores health management information 500. The health management information 500 is information for managing the body information, the matching information, and the input action information of the user 100. To facilitate the description, the health management information 500 is divided into two pieces of information, but the actual health management information 500 is managed as one table. Note that the health management information 500 of each user 100 is stored in the database 150 according to the first embodiment.

The health management information 500 includes entries including a measurement time 501, an ID 502, a type of measurement instrument 503, a type of body information 504, body information 505, an elapsed time 506, an input time 507, the number of corrections 508, a matching result 509, the number of repetitions 510, and the number of items 511.

The measurement time 501, the ID 502, the type of measurement instrument 503, and the type of body information 504 are fields in which values included in the meta-information granted to the first body information are stored. The body information 505 is a field in which the first body information is stored. The elapsed time 506, the input time 507, and the number of corrections 508 are fields in which values included in the input action information are stored. The matching result 509 is a field in which values included in the matching information is stored.

The number of repetitions 510 and the number of items 511 are fields in which values are stored when the measurement instrument 110 repeatedly measures the same types of body information during one set measurement period after starting measurement. The one set measurement period is, for example, a period from one hour to two hours from the start of the measurement.

Here, each of the fields included in the entries will be described.

The measurement time 501 is a field in which a time at which measurement of the first body information is completed is stored. Note that a time at which the terminal 120 receives the first body information may be stored in the measurement time 501. The ID 502 is a field in which identification numbers granted to the measurement instruments 110 are stored. The type of measurement instrument 503 is a field in which types of measurement instruments 110 are stored. The type of body information 504 is a field in which types of body information measured by the measurement instruments 110 are stored. The body information 505 is a field in which body information (second body information) measured by the measurement instrument 110 is stored.

The elapsed time 506 is a field in which an elapsed time from completion of the measurement of the first body information and start of an input of the second body information is stored. For example, when a time at which the measurement of the first body information is completed is "13:00:10" and a time at which an input of the second body information starts is "14:00:31," "1.0" is stored in the elapsed time 506. Note that a value in units of hours is stored as a unit of the elapsed time 506 according to the present embodiment.

The input time 507 is a field in which a time from start of an input of the second body information by the user 100 operating the terminal 120 and end of the input is stored. For example, when a start time of an input of the second body information is "14:00:31" and an end time of the input of the second body information is "14:03:52," "00:03:21" is stored in the input time 507.

The number of corrections 508 is a field in which the number of times the body information is corrected in an operation of inputting the second body information is stored.

The matching result 509 is a field in which the matching information is stored. One of "TRUE" and "FALSE" is stored in the matching result 509. "TRUE" indicates that the first body information matches the second body information. "FALSE" indicates that the first body information does not match the second body information.

The number of repetitions 510 is a field in which the number of times the body information is measured during one set measurement period is stored. The number of items 511 is a field in which the number of types of body information measured during one set measurement period is stored.

Figure 6:
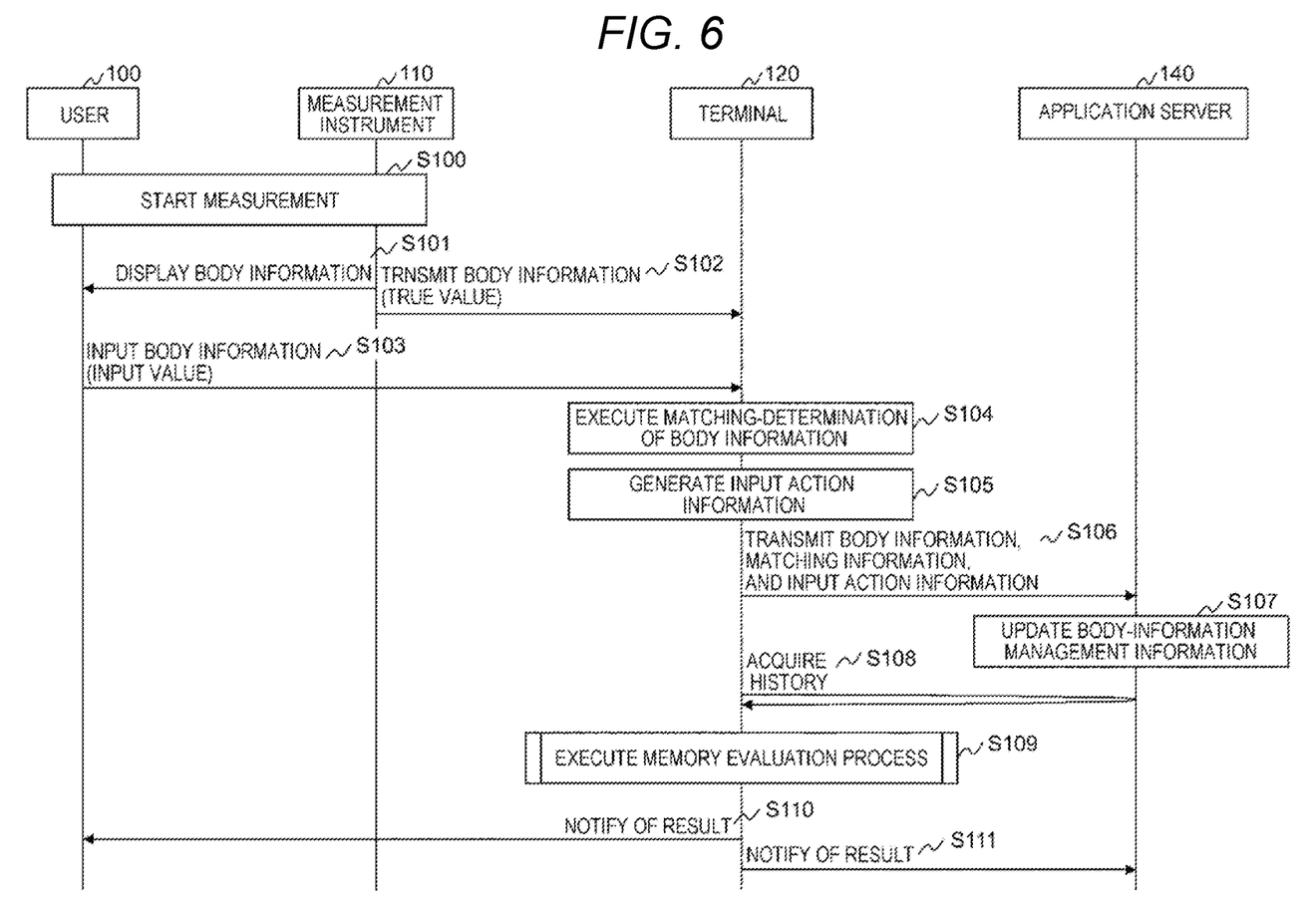
FIG. 6 is a sequence diagram illustrating a flow of a process of a computer system according to the first embodiment.

FIG. 6 is a sequence diagram illustrating a flow of a process of a computer system according to the first embodiment.

The user 100 starts measuring body information using the measurement instrument 110 (step S100).

The measurement instrument 110 displays the body information on the display screen 111 when the measurement of the body information is completed (step S101). Then, the measurement instrument 110 transmits the body information (the first body information) to the terminal 120 (step S102). Note that meta-information is added to the first body information transmitted by the measurement instrument 110.

The analysis module 310 of the terminal 120 temporarily stores the first body information in the memory 301. The analysis module 310 starts measuring an elapsed time using a measurement completion time included in the meta-information of the first body information as a starting point time.

The user 100 memorizes the body information displayed on the display screen 111 and inputs the body information (the second body information) to the terminal 120 at any timing (step S103).

When the second body information is received, the analysis module 310 of the terminal 120 executes a matching-determination process for the first body information and the second body information (step S104).

Specifically, the analysis module 310 determines whether the second body information matches the first body information. When the analysis module 310 determines that the second body information matches the first body information, the analysis module 310 outputs "TRUE" as matching information. When the analysis module 301 determines that the second body information does not match the first body information, the analysis module 310 outputs "FALSE" as matching information.

The terminal 120 generates the input action information (step S105). Specifically, the following process is executed.

The analysis module 310 calculates an elapsed time based on the starting time and a starting point time of the input operation of the user 100. The analysis module 310 calculates an input time based on the start time and the end time of the operation of inputting the second body information.

Then, the analysis module 310 counts the number of corrections of the body information in the operation of inputting the second body information. For example, the analysis module 310 counts the number of times a correction button is operated as the number of corrections of the body information.

The analysis module 310 generates the elapsed time, the input time, and the number of corrections as one piece of input action information. The process of step S105 has been described above.

The analysis module 310 of the terminal 120 transmits a registration request including the first body information, the matching result, and the input action information to the application server 140 (step S106).

When the application server 140 receives the registration request, the application server 140 updates the health management information 500 stored in the database 150 (step S107).

Specifically, the application 410 adds an entry to the health management information 500. The application 410 sets values in the measurement time 501, the ID 502, the type of measurement instrument 503, the type of body information 504, and the body information 505 of the added entry based on the first body information. The application 410 sets values in the elapsed time 506, the input time 507, and the number of corrections 508 of the added entry based on the input action information. The application 410 sets a value in the matching result 509 of the added entry based on the matching information.

Note that the application 410 may notify the terminal 120 that the updating of the health management information 500 is completed when the updating of the health management information 500 is completed.

The analysis module 310 of the terminal 120 transmits an acquisition request for acquiring a history (entry group) from the health management information 500 to the application server 140 (step S108). The acquisition request includes an identification number of the measurement instrument 110, a type of body information, and an acquisition period. The acquisition period is, for example, a period from the present time to a time before one month. Note that the acquisition period can be changed at any timing by the user or a manager or the like supplying the health service.

When the application server 140 receives the acquisition request, the application server 140 reads the entry group in which the measurement time 501 is included in the acquisition period from the health management information 500 and transmits a response including the read entry group to the terminal 120.

The analysis module 310 of the terminal 120 executes the memory evaluation process using the acquired entry group (step S109). The details of the memory evaluation process will be described with reference to FIG. 7.

The analysis module 310 of the terminal 120 notifies each of the measurement instrument 110 and the application server 140 of a processing result (steps S110 and S111).

When the application server 140 receives the processing result indicating that an outbreak risk of dementia is high, the application server 140 may notify a person such as a family member related to the user 100 of an analysis result or may notify a medical organization and a finance organization or the like of the analysis result. In this case, the user 100 designates a person, an organization, and a service that is notified of a processing result in advance by using a GUI.

Figure 7:
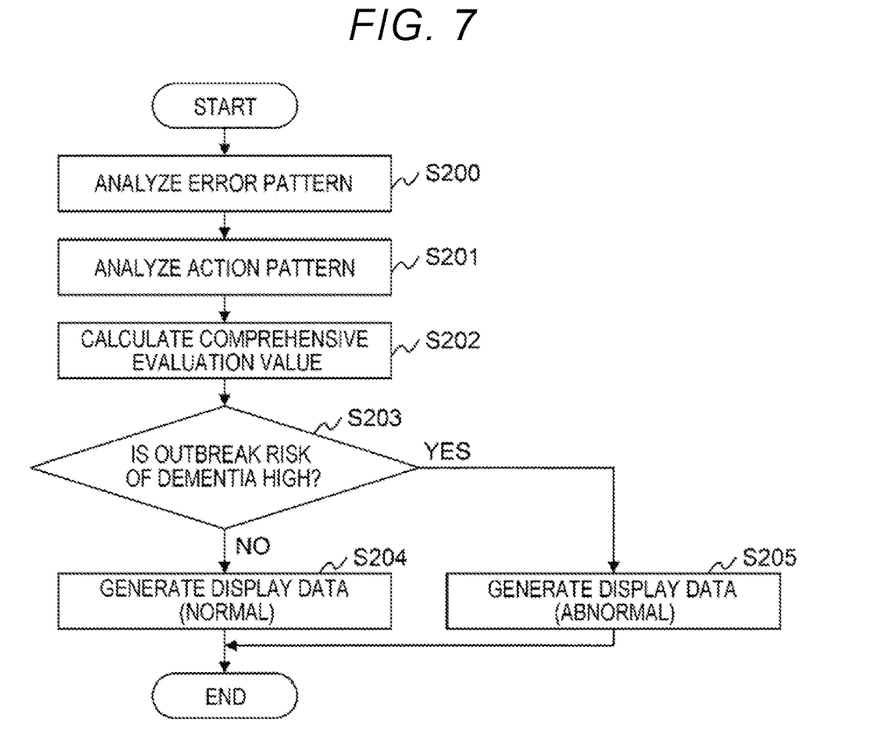
FIG. 7 is a flowchart illustrating an example of a process executed by an analysis module of the terminal according to the first embodiment.
Figure 8:
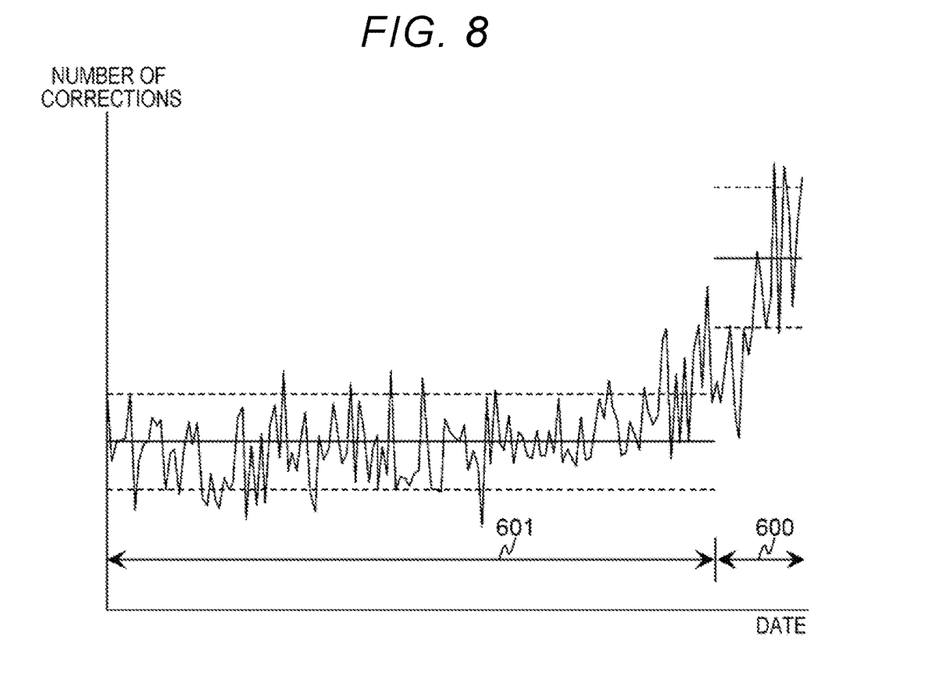
FIG. 8 is a diagram illustrating an example of a history of health management information acquired by the terminal according to the first embodiment.

FIG. 7 is a flowchart illustrating an example of the memory evaluation process executed by the analysis module 310 of the terminal 120 according to the first embodiment. FIG. 8 is a diagram illustrating an example of the history of the health management information 500 acquired by the terminal 120 according to the first embodiment.

The analysis module 310 analyzes an error pattern based on the entry group read from the health management information 500 (step S200). The error pattern is a pattern regarding the number of times the second body information different from the first body information is input, that is, a pattern regarding the number of times erroneous body information is input. From a different viewpoint, the error pattern serves as an index indicating a temporal change in the number of times erroneous body information is input.

When dementia occurs, the number of times the erroneous second body information is input increases due to deterioration in a short-term memory ability. From a different viewpoint, it is indicated that a probability (an error ratio) of the second body information not matching the first body information increases. Accordingly, the analysis module 310 analyzes a change in the error ratio. As a method of analyzing the error pattern, for example, the following process is considered.

The analysis module 310 calculates a ratio (a first error ratio) of entries in which the matching result 509 is "FALSE" among the entry groups included in a latest period. The latest period is, for example, a period from the present time to a time before one week. The analysis module 310 calculates a ratio (a second error ratio) of entries in which the matching result 509 is "FALSE" among the entry groups included in a period from the acquisition period excluding the latest period.

The analysis module 310 calculates a change amount of the error ratio by subtracting the first error ratio from the second error ratio. The analysis module 310 calculates a first evaluation value for evaluating memory based on the change amount of the error ratio. In the present embodiment, an expression in which the change amount of the error ratio is a variable is assumed to be set in advance.

When the change amount of the error ratio is positive, the short-term memory ability of the user 100 is estimated to deteriorate. In this case, the first evaluation value indicating that the memory deteriorates is calculated. The process of step S200 has been described above.

Subsequently, the analysis module 310 analysis an action pattern based on the entry group read from the health management information 500 (step S201). The action pattern is a pattern regarding an operation of inputting the second body information. From a different viewpoint, the action pattern serves as an index indicating a temporal change of the operation of inputting the second body information.

When dementia occurs, the body information is frequently corrected due to the deterioration in the short-term memory ability. Therefore, a time necessary to input the body information becomes longer. Accordingly, the analysis module 310 analyzes the number of corrections and the change in the input time in the operation of inputting the second body information.

When symptoms of dementia progress, a tendency to forget the input action of the second body information increases. Accordingly, the analysis module 310 analyzes a change in the elapsed time.

As a method of analyzing each value, for example, the following process is considered.

The analysis module 310 calculates an average value (a first evaluation value) of the input time 507 and the number of corrections 508 of the entry group included in a latest period. The analysis module 310 calculates an average value (a second evaluation value) of the input time 507 and the number of corrections 508 of the entry group included in the period from the acquisition period excluding the latest period.

The analysis module 310 calculates a change amount of the input time by subtracting the second average value from the first average value of the input time 507. The analysis module 310 calculates the change amount of the number of corrections by subtracting the second average value from the first average value of the number of corrections 508. The analysis module 310 calculates a second evaluation value for evaluating the memory based on a change amount of the input time and calculates a third evaluation value for evaluating the memory based on a change amount of the number of corrections. In the present embodiment, an expression in which each change amount is a variable is assumed to be set in advance.

Note that the analysis module 310 may calculate an evaluation value for evaluating the memory based on the change amount of the input time and the change amount of the number of corrections. Instead of the average value, a standard deviation may be used.

Note that an average value and a standard deviation of two periods are calculated as a value illustrated in FIG. 8. A period 800 indicates a latest period and a period 801 indicates a period from the acquisition period excluding the latest period. A solid line during each period indicates an average value and a dotted line during each period indicates a standard deviation.

When the change amount of the input time or the change amount of the number of corrections is positive, the short-term memory ability of the user 100 is estimated to deteriorate. In this case, the second evaluation value or the third evaluation value indicating that the memory deteriorates is calculated.

The analysis module 310 calculates an average value (a third average value) of the elapsed time 506 of the entry group included in the latest period. The analysis module 310 calculates an average value (a fourth average value) of the elapsed time 506 of the entry group included in a period from the acquisition period excluding the latest period.

The analysis module 310 calculates a change amount of an elapsed time by subtracting the fourth average value from the third average value. The analysis module 310 calculates a fourth evaluation value for evaluating the memory based on the change amount of the elapsed time. In the present embodiment, an expression in which a change amount of the elapsed time is a variable is assumed to be set in advance.

When the change amount of the elapsed time is positive, symptoms of dementia are estimated to progress. In this case, the fourth evaluation value indicating that the memory deteriorates is calculated. The process of step S201 has been described above.

Subsequently, the analysis module 310 calculates a comprehensive evaluation value (step S202). Specifically, the analysis module 310 calculates the comprehensive evaluation value based on the evaluation value calculated in step S200 and the evaluation value calculated in step S201.

For example, the analysis module 310 calculates a sum value of all the evaluation values as the comprehensive evaluation value. The analysis module 310 calculates the comprehensive evaluation value by adding values obtained by multiplying each evaluation value by a weighting coefficient.

Subsequently, the analysis module 310 determines whether the outbreak risk of dementia is high based on the comprehensive evaluation value (step S203). For example, the analysis module 310 compares the comprehensive evaluation value to a threshold. When the comprehensive evaluation value is greater than the threshold, the analysis module 310 determines that the outbreak risk of dementia is high.

When the analysis module 310 determines that the outbreak risk of dementia is low, the analysis module 310 generates display data for notifying that the outbreak risk of dementia is low (step S204) and ends the process. Note that when the outbreak risk of dementia is low, the analysis module 310 may not generate the display data. In this case, the user 100 and the application server 140 are not notified of the display data.

When the analysis module 310 determines that the outbreak risk of dementia is high, the analysis module 310 generates display data for notifying that the outbreak risk of dementia is high (step S205) and ends the process.

Note that the analysis module 310 may merely analyze the error pattern or may merely execute the action pattern. In the analysis of the action pattern, one of the elapsed time 506, the input time 507, and the number of corrections 508 may be executed.

According to the above-described first embodiment, the user 100 using the system supplying the health service can ascertain the outbreak risk of dementia when the body information is measured using the measurement instrument 110. In the present embodiment, since it is not necessary to use an examination method and system specialized for evaluating a cognitive function, dementia can be diagnosed without imposing a burden on the user.

Since the outbreak risk of dementia is estimated based on a statistical process, an abnormal value of a specific time can be excluded. Therefore, accurate dementia diagnosis can be carried out. In the first embodiment, since relative evaluation is executed, dementia can be diagnosed according to the memory and a body ability of the user 100.

Second Embodiment

A second embodiment differs in a configuration of a computer system. Hereinafter, the second embodiment will be described focusing on differences from the first embodiment.

Figure 9:
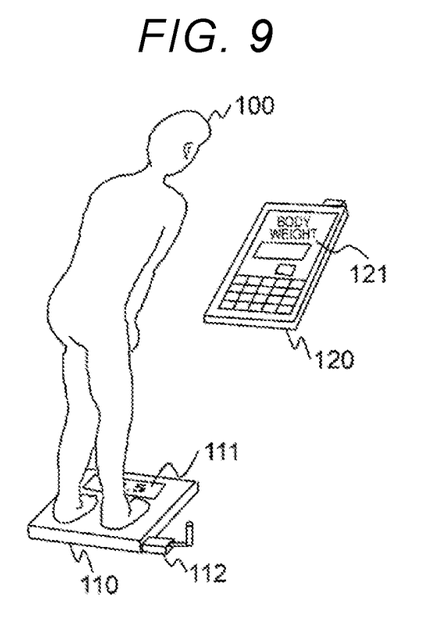
FIG. 9 is a diagram illustrating a configuration example of a computer system according to a second embodiment.
Figure 10:
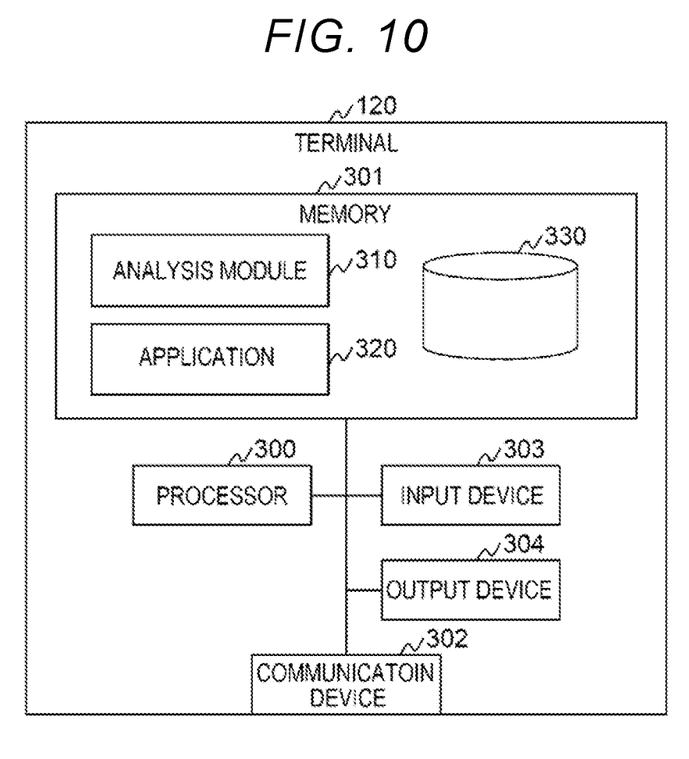
FIG. 10 is a diagram illustrating an example of a hardware configuration and a software configuration of a terminal according to the second embodiment.

FIG. 9 is a diagram illustrating a configuration example of the computer system according to the second embodiment. FIG. is a diagram illustrating an example of a hardware configuration and a software configuration of a terminal 120 according to the second embodiment.

The computer system according to the second embodiment includes a measurement instrument 110 and a terminal 120. In the second embodiment, the terminal 120 supplies a health service.

The terminal 120 according to the second embodiment has the same hardware configuration as the terminal 120 according to the first embodiment. The terminal 120 according to the second embodiment has a different software configuration from the terminal 120 according to the first embodiment. Specifically, the memory 301 stores a program that realizes an application 320 besides the analysis model 310. The database 330 is stored in the memory 301. The application 320 has the same function as the application 410. The database 330 stores the health management information 500 of the user 100 operating the terminal 120.

Note that the terminal 120 may include a storage device that stores the database 330. In consideration of the capacity of the memory 301 of the terminal 120, an entry stored in the health management information 500 may be deleted after a given period is elapsed.

Figure 11:
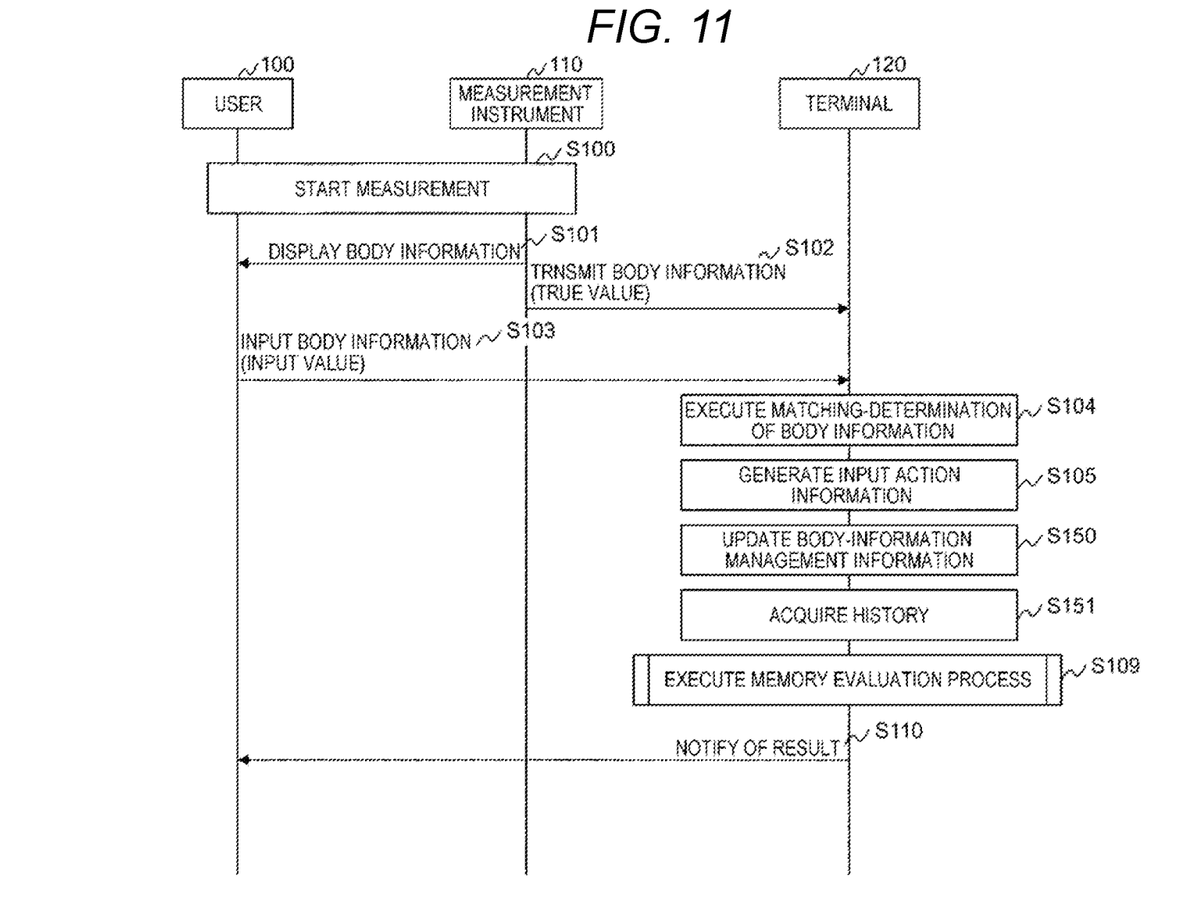
FIG. 11 is a sequence diagram illustrating a flow of a process of a computer system according to the second embodiment.

FIG. 11 is a sequence diagram illustrating a flow of a process of a computer system according to the second embodiment.

The processes from step S100 to step S105 are the same as those of the first embodiment. The analysis module 310 updates the health management information 500 by outputting a registration request including the first body information, the matching result, and the input action information to the application 320 after the input action information is generated (step S150). The analysis module 310 acquires a history from the database 330 (step S151).

The processes of steps S109 and S110 are the same as those of the first embodiment. In the second embodiment, since the application server 140 is not located, the process of step S111 is not executed.

According to the second embodiment, the same advantages as those of the first embodiment can be obtained in the system in which the terminal 120 supplies the health service.

Third Embodiment

A third embodiment differs in a configuration of the measurement instrument 110. Hereinafter, the third embodiment will be described focusing on differences from the first embodiment.

Figure 12:
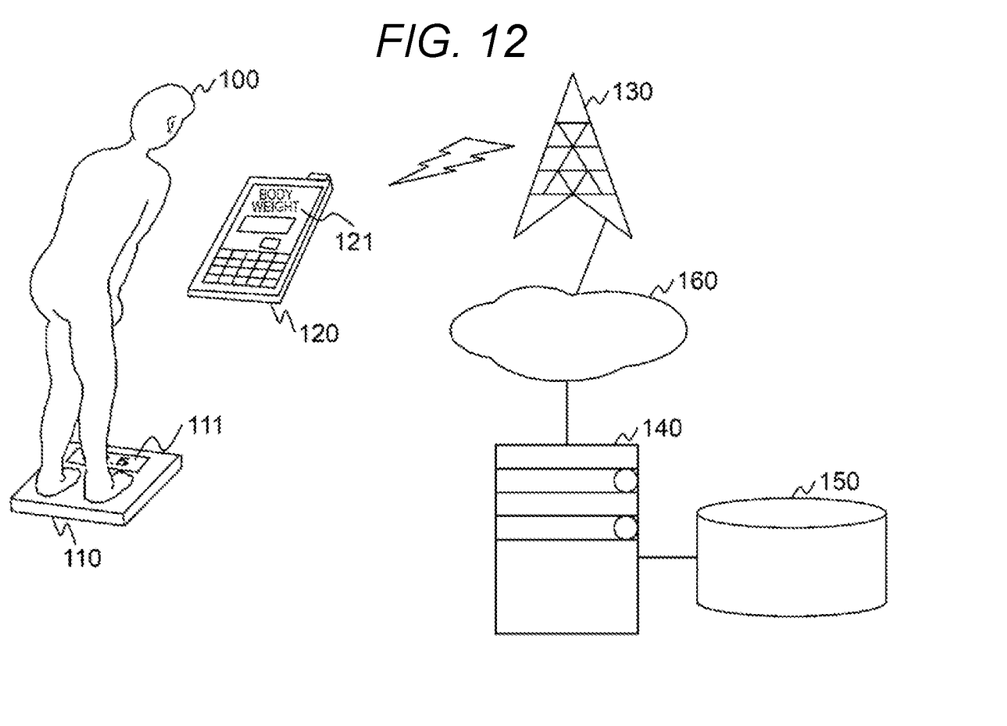
FIG. 12 is a diagram illustrating a configuration example of a computer system according to a third embodiment.

FIG. 12 is a diagram illustrating a configuration example of a computer system according to the third embodiment.

The computer system according to the third embodiment includes a measurement instrument 110, a terminal 120, a base station 130, an application server 140, and a database 150 as in the computer system according to the first embodiment.

In the third embodiment, the measurement instrument 110 does not include the communication device 402. The other remaining configuration of the device according to the third embodiment is the same as that of the first embodiment.

In the third embodiment, a data structure of the health management information 500 differs. Specifically, the body information 505 and the matching result 509 are not included in the entries. This is because the measurement instrument 110 may not transmit the first body information in the third embodiment.

A memory evaluation process of the third embodiment partially differs. Specifically, the process of step S200 is not executed. This is because the health management information 500 does not include the matching result 509.

According to the third embodiment, even though the measurement instrument 110 does not include the communication device 112, the same advantages as those of the first embodiment can be obtained.

Note that the invention is not limited to the foregoing embodiments and includes various modification examples. For example, in the foregoing embodiments, the configurations have been described in detail to facilitate the description of the invention and all the described configurations may not necessarily be included. Some of the configurations according to each embodiment may be added to, deleted from, or substituted with other configurations.

Some or all of the foregoing configurations, functions, processing units, and processing mechanisms, and the like may be realized by hardware, for example, by designing integrated circuits or the like. The invention can also be realized by a program code of software that realizes the functions of the embodiments. In this case, a storage medium that records the program code is supplied to a computer and a processor included in the computer reads the program code stored in the storage medium. In this case, the program code read from the storage medium realizes the functions of the above-described embodiments, and the program code and the storage medium storing the program code embody the invention. As the storage medium supplying the program code, for example, a flexible disc, a CD-ROM, a DVD-ROM, a hard disk, a solid state drive (SSD), an optical disc, a magneto-optical disc, a CD-R, a magnetic tape, a nonvolatile memory card, or a ROM is used.

The program code realizing the functions described in the present embodiment can be mounted in, for example, any of a wide range of programs or script languages such as Assembler, C/C++, perl, Shell, PHP, and Java (registered trademark).

Further, the program code of software realizing the functions according to the embodiment may be delivered via a network, the program code may be stored in a storage such as a hard disk or a memory mechanism of a computer or a storage medium such as a CD-RW or a CD-R, so that a processor included in the computer reads the program code stored in the storage mechanism or the storage medium and executes the program code.

In the above-described embodiments, control lines or information lines considered to be necessary for description are illustrated and all the control lines or information lines are not necessarily illustrated for a product. All the configurations may be mutually connected.

What is claimed is:

1. An automated computer system for accurately evaluating a diagnosis of at least one of dementia and Alzheimer's disease in a user, that supplies a health service using body information of the user measured by a measurement instrument, the computer system comprising:
   a computer that includes an analysis unit analyzing a cognitive function of the user, wherein
   the cognitive function includes at least one of an outbreak risk of dementia and Alzheimer's disease,
   the computer includes a processor, a memory connected to the processor, and a network interface connected to the processor,
   the processor is connected to be accessible to a storage device that stores first body information which is the body information transmitted by the measurement instrument, and
   the analysis unit is configured to
      acquire the first body information and second body information which is body information presented by the measurement instrument and memorized by the user,
      execute a matching-determination process of determining whether the second body information matches the first body information,
      generate input action information which is information regarding an input action of the second body information by the user,
      register the first body information in the storage device in association with a result of the matching-determination process and the input action information,
      acquire histories of the result of the matching-determination process and the input action information from the storage device,
      calculate a first error ratio based on the number of times the first body information different from the second body information in a first predetermined period which is a latest period,
      calculate a second error ratio based on the number of times the first body information different from the second body information in a second predetermined period, wherein the second predetermined period includes the histories and does not include the first predetermined period, calculate an error pattern based on the first error ratio and the second error ratio, calculate a first value of the input action information from the first predetermined period, calculate a second value of the input action information from the second predetermined period, calculate an action pattern based on the first value and the second value, calculate, from the action pattern, a first evaluation value for evaluating the cognitive function and a second evaluation value for evaluating the cognitive function, calculate a third evaluation value based on a change in the first evaluation value and the second evaluation value, calculate a comprehensive evaluation based on the error pattern and the third evaluation value, and evaluate the cognitive function of the user based on the comprehensive evaluation by comparing the comprehensive evaluation to a threshold value, wherein on a condition that the comprehensive evaluation is less than the threshold value, the outbreak risk of at least one of dementia and Alzheimer's disease is low, and wherein on a condition that the comprehensive evaluation is greater than the threshold value, the outbreak risk of at least one of dementia and Alzheimer's disease is high.

2. The computer system according to claim 1, wherein the input action information includes the number of corrections at the time of inputting the second body information, and the analysis unit is configured to supply an interface for inputting the second body information, measure the number of corrections at the time of inputting the second body information using the interface, and analyze a pattern related to the number of corrections at the time of inputting the second body information as the action pattern.

3. The computer system according to claim 1, wherein the input action information includes an input time which is a time from start to end of the input of the second body information, and the analysis unit is configured to supply an interface for inputting the second body information, measure the input time at the time of inputting the second body information using the interface, and analyze a pattern related to the input time as the action pattern.

4. The computer system according to claim 1, wherein the input action information includes an elapsed time which is a time from completion of measurement of the first body information to start of an input of the second body information, and the analysis unit is configured to supply an interface for inputting the second body information, calculate the elapsed time based on a measurement time included in the first body information and a time at which the second body information starts to be input using the interface, and analyze a pattern related to the elapsed time as the action pattern.

5. The computer system according to claim 2, wherein the analysis unit determines whether the outbreak risk of at least one of dementia and Alzheimer's disease based on a result of evaluation of the cognitive function of the user is high, and when the outbreak risk of at least one of dementia and Alzheimer's disease is determined to be high, the analysis unit notifies at least one of the user, a person related to the user, and a system supplying a service contacted with the user that the outbreak risk of at least one of dementia and Alzheimer's disease is high.

6. A method of evaluating a cognitive function executed by an automated computer system for accurately evaluating a diagnosis of at least one of dementia and Alzheimer's disease in a user, that supplies a health service using body information of a user measured by a measurement instrument, the computer system including a computer that includes an analysis unit analyzing a cognitive function of the user, wherein the cognitive function includes at least one of an outbreak risk of dementia and Alzheimer's disease, the computer including a processor, a memory connected to the processor, and a network interface connected to the processor, the processor being connected to be accessible to a storage device that stores first body information which is body information transmitted by the measurement instrument, the method of evaluating the cognitive function comprising:

acquiring, via the analysis unit, the first body information and second body information which is body information presented by the measurement instrument and memorized by the user;

executing, via the analysis unit, a matching-determination process of determining whether the second body information matches the first body information;

generating, via the analysis unit, input action information which is information regarding an input action of the second body information by the user, registering, via the analysis unit, the first body information in the storage device in association with a result of the matching-determination process and the input action information, acquiring, via the analysis unit, histories of the result of the matching-determination process and the input action information from the storage device, calculating, via the analysis unit, a first error ratio based on the number of times the first body information different from the second body information in a first predetermined period which is a latest period, calculating, via the analysis unit, a second error ratio based on the number of times the first body information different from the second body information in a second predetermined period, wherein the second predetermined period includes the histories and does not include the first predetermined period, calculating, via the analysis unit, an error pattern based on the first error ratio and the second error ratio, calculating, via the analysis unit, a first value of the input action information from the first predetermined period, calculating, via the analysis unit, a second value of the input action information from the second predetermined period, calculating, via the analysis unit, an action pattern based on the first value and the second value, calculating, via the analysis unit, from the action pattern, a first evaluation value for evaluating the cognitive function and a second evaluation value for evaluating the cognitive function, calculating, via the analysis unit, a third evaluation value based on a change in the first evaluation value and the second evaluation value, calculating, via the analysis unit, a comprehensive evaluation based on the error pattern and the third evaluation value, and evaluating, via the analysis unit, the cognitive function of the user based on the comprehensive evaluation by comparing the comprehensive evaluation to a threshold value, wherein on a condition that the comprehensive evaluation is less than the threshold value, the outbreak risk of at least one of dementia and Alzheimer's disease is low, and wherein on a condition that the comprehensive evaluation is greater than the threshold value, the outbreak risk of at least one of dementia and Alzheimer's disease is high.

7. The method of evaluating the cognitive function according to claim 6, wherein the input action information includes the number of corrections at the time of inputting the second body information, the analysis unit supplies an interface for inputting the second body information, measuring, by the analysis unit, the number of corrections at the time of inputting the second body information using the interface, and analyzing, by the analysis unit, a pattern related to the number of corrections at the time of inputting the second body information as the action pattern.

8. The method of evaluating the cognitive function according to claim 6, wherein the input action information includes an input time which is a time from start to end of the inputting of the second body information, the analysis unit supplies an interface for inputting the second body information, measuring, by the analysis unit, the input time at the time of inputting the second body information using the interface, and analyzing, by the analysis unit, a pattern related to the input time as the action pattern.

9. The method of evaluating the cognitive function according to claim 6, wherein the input action information includes an elapsed time which is a time from completion of measurement of the first body information to start of an input of the second body information, the analysis unit supplies an interface for inputting the second body information, calculating, by the analysis unit, the elapsed time based on a measurement time included in the first body information and a time at which the second body information starts to be input using the interface, and analyzing, by the analysis unit, a pattern related to the elapsed time as the action pattern.

10. The method of evaluating the cognitive function according to claim 7, further comprising:

determining, by the analysis unit, whether the outbreak risk of at least one of dementia and Alzheimer's disease is high based on a result of evaluation of the cognitive function of the user; and when the outbreak risk of at least one of dementia and Alzheimer's disease is determined to be high, notifying at least one of the user, a person related to the user, and a system supplying a service contacted with the user that the outbreak risk of at least one of dementia and Alzheimer's disease is high by the analysis unit.

11. A non-transitory computer-readable medium storing a program on a computer including a processor, a memory connected to the processor, and a network interface connected to the processor, the automated computer for accurately evaluating a diagnosis of at least one of dementia and Alzheimer's disease in a user, which supplies a health service using body information of a user measured by a measurement instrument, the processor being connected to be accessible to a storage device that stores first body information which is body information transmitted by the measurement instrument, when executed by a processor causes the processor to:

acquiring the first body information and second body information which is body information presented by the measurement instrument and memorized by the user, executing a matching-determination process of determining whether the second body information matches the first body information, generating input action information which is information regarding an input action of the second body information by the user, registering the first body information in the storage device in association with a result of the matching-determination process and the input action information, acquiring histories of the result of the matching-determination process and the input action information from the storage device, calculating a first error ratio based on the number of times the first body information different from the second body information in a first predetermined period which is a latest period, calculating a second error ratio based on the number of times the first body information different from the second body information in a second predetermined period, wherein the second predetermined period includes the histories and does not include the first predetermined period, calculating an error pattern based on the first error ratio and the second error ratio, calculating a first value of the input action information from the first predetermined period, calculating a second value of the input action information from the second predetermined period, calculating an action pattern based on the first value and the second value, calculating, from the action pattern, a first evaluation value for evaluating a cognitive function of the user and a second evaluation value for evaluating the cognitive function, calculating a third evaluation value based on a change in the first evaluation value and the second evaluation value, calculating a comprehensive evaluation based on the error pattern and the third evaluation value, and evaluating the cognitive function of the user based on the comprehensive evaluation by comparing the comprehensive evaluation to a threshold value, wherein on a condition that the comprehensive evaluation is less than the threshold value, the outbreak risk of at least one of dementia and Alzheimer's disease is low, and wherein on a condition that the comprehensive evaluation is greater than the threshold value, the outbreak risk of at least one of dementia and Alzheimer's disease is high, and wherein the cognitive function includes at least one of an outbreak risk of dementia and Alzheimer's disease.

12. The program according to claim 11, wherein
the input action information includes the number of corrections at the time of inputting the second body information,
the computer supplies an interface for inputting the second body information,
measuring the number of corrections at the time of inputting the second body information using the interface, and
analyzing a pattern related to the number of corrections at the time of inputting the second body information as the action pattern.

13. The program according to claim 11, wherein
the input action information includes an input time which is a time from start to end of the input of the second body information,
the computer supplies an interface for inputting the second body information,
measuring the input time at the time of inputting the second body information using the interface, and
analyzing a pattern related to the input time as the action pattern.

14. The program according to claim 11, wherein
the input action information includes an elapsed time which is a time from completion of measurement of the first body information to start of an input of the second body information,
the computer supplies an interface for inputting the second body information,
calculating the elapsed time based on a measurement time included in the first body information and a time at which the second body information starts to be input using the interface, and
analyzing a pattern related to the elapsed time as the action pattern.

15. The program according to claim 12, the program causing the computer to further execute:
determining whether the outbreak risk of at least one of dementia and Alzheimer's disease based on a result of evaluation of memory of the user is high, and
when the outbreak risk of at least one of dementia and Alzheimer's disease is determined to be high, notifying at least one of the user, a person related to the user, and a system supplying a service contacted with the user that the outbreak risk of at least one of dementia and Alzheimer's disease is high.

* * * * *